(12) United States Patent
Lambert

(10) Patent No.: US 6,811,541 B2
(45) Date of Patent: Nov. 2, 2004

(54) TRACTION DEVICE

(76) Inventor: Dennis Michael Lambert, 9029 Biplane Way, Fair Oaks, CA (US) 95628

( * ) Notice: Subject to any disclaimer, the term of this patent is extended or adjusted under 35 U.S.C. 154(b) by 189 days.

(21) Appl. No.: 10/154,360

(22) Filed: May 23, 2002

(65) Prior Publication Data

US 2003/0220595 A1 Nov. 27, 2003

(51) Int. Cl.[7] .................................................. A61F 5/00
(52) U.S. Cl. .............................. 602/36; 602/32; 602/35
(58) Field of Search ............................. 602/36, 32, 35, 602/38, 20, 22; 128/878, 879, 880, 876

(56) References Cited

U.S. PATENT DOCUMENTS

| | | | |
|---|---|---|---|
| 2,584,203 A | | 2/1952 | Hart |
| 2,590,739 A | * | 3/1952 | Wagner et al. ................ 602/39 |
| 3,693,617 A | | 9/1972 | Trott |
| 3,850,166 A | | 11/1974 | Tamny et al. |
| 3,872,861 A | * | 3/1975 | Tamny et al. ................. 602/36 |
| 4,445,506 A | | 5/1984 | Johansson et al. |
| 5,074,291 A | | 12/1991 | Carter |
| 5,127,898 A | * | 7/1992 | McConnelll ................. 602/36 |
| 5,156,168 A | | 10/1992 | Canterna |
| 5,387,186 A | * | 2/1995 | Edland ........................ 602/36 |
| 5,441,480 A | * | 8/1995 | Kane et al. ................... 602/36 |
| 5,451,203 A | * | 9/1995 | Lamb .......................... 602/36 |
| 5,735,806 A | | 4/1998 | Leibovic |
| 6,467,487 B1 | * | 10/2002 | Rios ........................... 128/869 |

* cited by examiner

Primary Examiner—Henry Bennett
Assistant Examiner—Amanda Flynn
(74) Attorney, Agent, or Firm—James M. Ritchey

(57) ABSTRACT

An traction apparatus for use in manipulating a patient's arm and wrist bones comprises a traction assembly having a plurality of finger traps, a plurality of springs with each spring capable of releasably associating with at least one trap, and a swivel base secured to each of the springs. Also, included are a traction force scale coupled to the traction assembly, a first traction force generating mechanism linked to the traction force scale, a second traction force generating mechanism coupled to the patient's upper arm, and a support attachment system for securing the subject apparatus components to a support. Additionally, a spacer for separating and positioning the patient's fingers is included.

22 Claims, 9 Drawing Sheets

TRACTION DEVICE

BACKGROUND OF THE INVENTION

1. Field of the Invention

A bone manipulation or traction device is disclosed. More specifically, the subject device easily permits a practitioner to manipulate damaged arm bones including an ulna and/or radius.

2. Description of the Background Art

Several traction devices exist, but each one fails to be of practical use in many real-life situations. As seen in U.S. Pat. No. 2,584,203, the traction apparatus uses rubber tubing to apply traction. The use of rubber tubing, under some situations, presents possible dangers to the patient and operator. Pulling tension with rubber tubing could potentially be hazardous due to a significant possibility of rubber break-down and separation, since the rubber could be ripped easily, develop holes, or could simply tear while in use. Replacement of torn rubber tubing takes time and is inconvenient. With newer possible resilient means available this device appears outdated. Further, this product is not portable in a user friendly way. Generally, this device either sits on the floor or on a table, thereby putting a patient several feet off the ground which is not ideal and usually impractical.

Disclosed in U.S. Pat. No. 5,074,291 is a device that involves a significant expense to fabricate. First, a user must purchase the related table and frame together. Second, this device may only be used in an operating room, since this invention was designed for surgery on the wrist or forearm. Many utilization options are precluded with this design.

U.S. Pat. No. 5,735,806 presents a wrist traction apparatus that is so simplified that it is not adjustable in many critical locations. Force is applied to both the thumb and a finger and if the operator wants to place added tension to the thumb, for alignment purposes, the finger next to the thumb experiences decreased tension. The novel subject design of the current applications has utility springs and quick release clips in place of the pulleys and ropes or cables, thus allowing the current subject system to pull traction with exact tension to all fingers used plus increase tension to any one digit safely and easily simple by taking the extra spring not used and clipping it to the spring of the finger that needs the extra tension. This could be used when an operator desires to align certain bones by pulling on one finger slightly harder. The technique is used often and it works quite well with the current subject devise, but is not possible with the '806 apparatus. A versatile system must have this feature to be effective. With the '806 tension apparatus the exact amount of force can not be determined. This could result is a possibly dangerous situation. The current subject system has a scale to present the force applied. Additionally, the traction pulley in the '806 apparatus is a relatively expensive "complete" component with no currently available parts for servicing.

Presented in U.S. Pat. No. 5,156,168 is a glove-like support for arthroscopy. Since arthroscopic type surgical procedures are only envisioned, in an operating room (OR) environment, this device would not work in a typical emergency room (ER) setting. The current subject apparatus may be utilized in both ER and OR settings and doesn't need a glove, which would need to be laundered.

Described in U.S. Pat. No. 4,445,506 is a bone aligning apparatus that is bulky and involves several time consuming fine-adjustments for use. Given the limited space available in a typical ER or OR environment, this apparatus would take up too much space and present a difficult cleaning problem. The fingers are placed into the finger holders, then an operator must manually adjust even tension once traction has begun which takes time. Further, with the '506 system there is no guarantee there will be an even distribution of traction to all of the secured fingers. The fixed position design not only restricts a patient's hand to that position only, which is not always needed, but the '506 device has not individual finger adjustments so it limits the hand to solely that position. The current subject system has a generally circular finger positioning design, with a spring suspension system that permits various hand alignment possibilities (utilizing a ball within the hand to generate a desired natural position). This is important, for the current subject invention, because it is a natural position for the hand and it becomes easier to align bones, especially when the thumb is needed in the reduction. The subject spring suspension allows among other things, freedom to move fingers into positions needed for other concentrated reductions.

U.S. Pat. No. 3,850,166 discloses a fracture reduction system that offers a wide range of configurations, but by presenting a wide range of configuration is overly complicated. With the '166 system there are a significant number of parts. If a part fails, it becomes complicated to replace them. Although the finger positioning can be adjusted manually, it does not allow for automatic finger tension adjustment simply by pulling traction, as in the current subject apparatus. Additionally, the '166 device would be difficult to clean and sterilize. The current subject device is easy to use and self adjusts for tension and all parts are designed to rapidly disassemble. With the current subject device extra tension may be added to any finger just by a simple clip.

U.S. Pat. Nos. 2,783,758 and 3,693,617 relate a fracture reducing device for the arm in which a table or table-like means supports the device. The arm is virtually fixed in a non-variable position and no automatic finger tension adjustment exists. Also, the traction device has only one finger trap, which could create undue stress on the finger (care must be taken of the associated ligaments and tendons in a hand and not to damage one by undue stress). Additionally, the necessity of having a sturdy table or table-like support limits the versatility of this devise, especially in spaces crowded with critical equipment. Further, in the '617 version a sandbag is utilized for downward force and is not adjustable.

The foregoing patents reflect the state of the art of which the applicant is aware and are tendered with the view toward discharging applicant's acknowledged duty of candor in disclosing information which may be pertinent in the examination of this application. It is respectfully submitted, however, that none of these patents teach or render obvious, singly or when considered in combination, applicants claimed invention.

SUMMARY OF THE INVENTION

An object of the present invention is to disclose an arm and wrist traction device that allows a single operator to manipulate bones in a patient arm and/or wrist in either an operation room or emergency room situation and mounts to any IV pole or similar support.

Another object of the present invention is to present an arm and wrist traction device that hooks to any IV pole and has five finger traps, which distributes weight evenly to all fingers trapped, and has a very simple, safe ratcheting system for counter traction and an easy to read scale that is position adjustable.

A further object of the present invention is to provide an arm and wrist traction apparatus that includes springs and quick release clips that allow an operator to pull traction with exact scale-determined tension to all of the secured fingers plus increase tension to any one finger safely and easily by taking a non-used spring and coupling it to the finger that needs extra tension.

Still another object of the present invention is to disclose an arm and wrist traction apparatus that easily disassembles for quick assembly, cleaning, repair, and/or sterilization.

Yet a further object of the present invention is to divulge an arm and wrist traction apparatus that is user/operator/physician friendly and comprises a plurality of finger traps mounted to a base via separate resilient means associated with each trap, a traction force measurement means, first and second traction force generating means, and support attachment means which allows the user/operator/physician to pose the patient's hand in various desirable/required positions.

Disclosed is a user friendly and easily assembled or dissembled arm and wrist traction apparatus that comprises a traction assembly having a plurality of finger traps mounted to a base via separate resilient means associated with each trap, a traction force measurement means coupled to the traction assembly, first and second traction force generating means, and support attachment means for securing the subject apparatus. The subject device is utilized by a user/operator that is, depending of the circumstance, a physician, nurse, or other qualified individual. The subject apparatus may be mounted to a dedicated vertical support or easily hooks on to any standard intravenous (IV) pole.

The first or upper traction force generating means commonly comprises a ratchet or equivalent means that adjusts easily and has an easy grip handle to apply traction. The first traction force is secured to the traction force measurement means. The traction force measurement means comprises, preferably, a scale marked in pounds (often a 50 lb scale is employed) and kilograms to monitor the exact traction force applied. Usually, the scale is placed between the first traction force generating means and the traction assembly.

The traction assembly comprises, a plurality of finger traps mounted to a swivel base. Each finger trap is releasably coupled to the swivel base via separate resilient means. Preferably, each resilient means, at least one associated with each finger trap, comprises an extendable spring. When a traction force is pulled, all fingers in traction (coupled within a finger trap) will pull evenly, without manual adjustment. Quick release clips associated with each spring allow finger traps to be easily and quickly interchangeable. Additionally springs can be clipped together to add selected extra tension for fingers, which might need added tension support.

The second or counter traction force generating means of the subject invention commonly consists of an adjustable padded cuff with a quick release clip, which fastens to the tension means, often a cable, cord, or rope, that runs through the ratchet that hooks to the bottom of the support/IV pole. Usually, the ratchet has a rope or a comfort handle to pull for second or counter traction force.

Other objects, advantages, and novel features of the present invention will become apparent from the detailed description that follows, when considered in conjunction with the associated drawings.

DESCRIPTION OF THE PREFERRED EMBODIMENT

Figure 1:
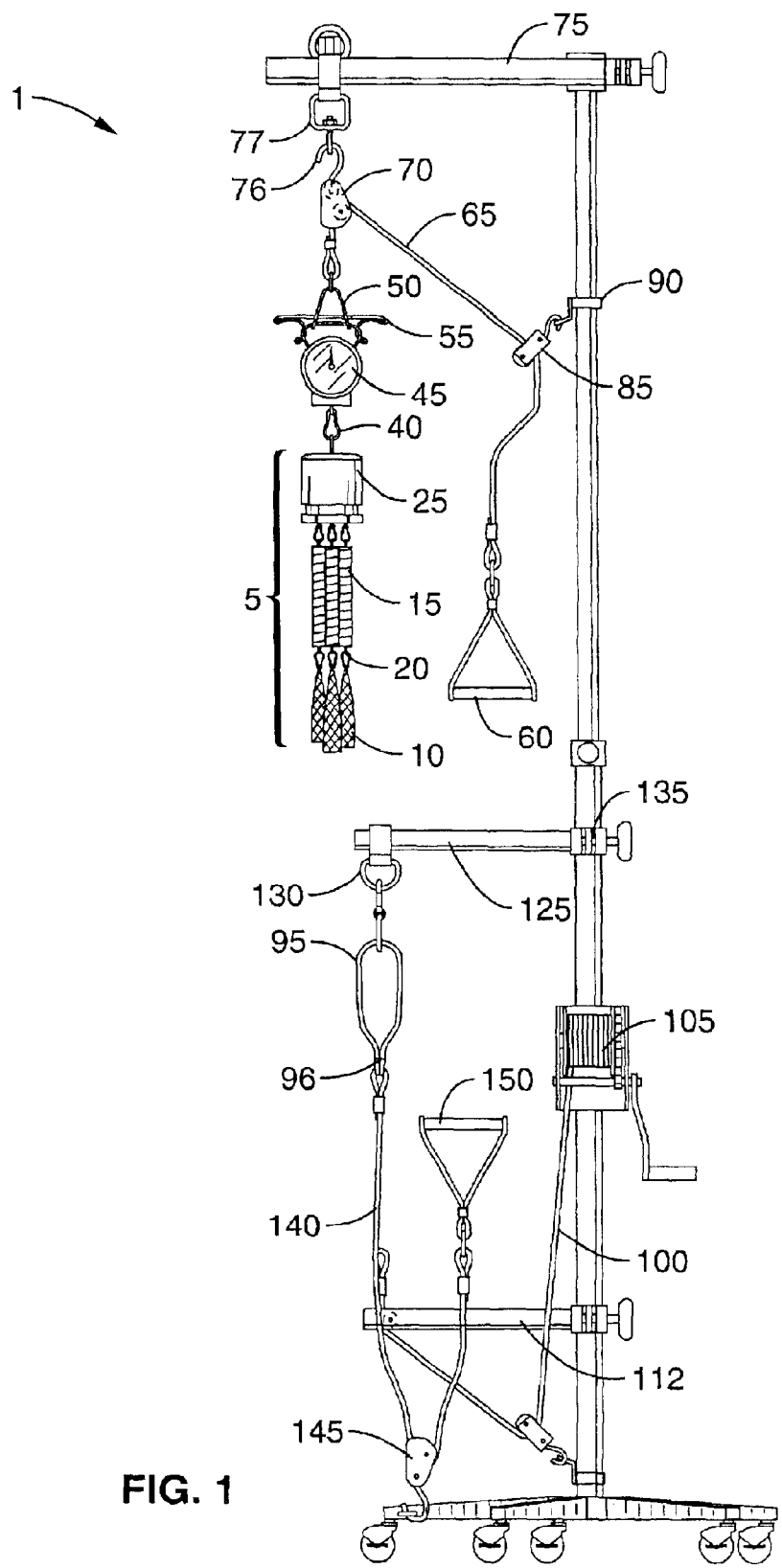
FIG. 1 is a front view of the subject invention showing both a first and second embodiments of the second traction force generating means.
Figure 2:
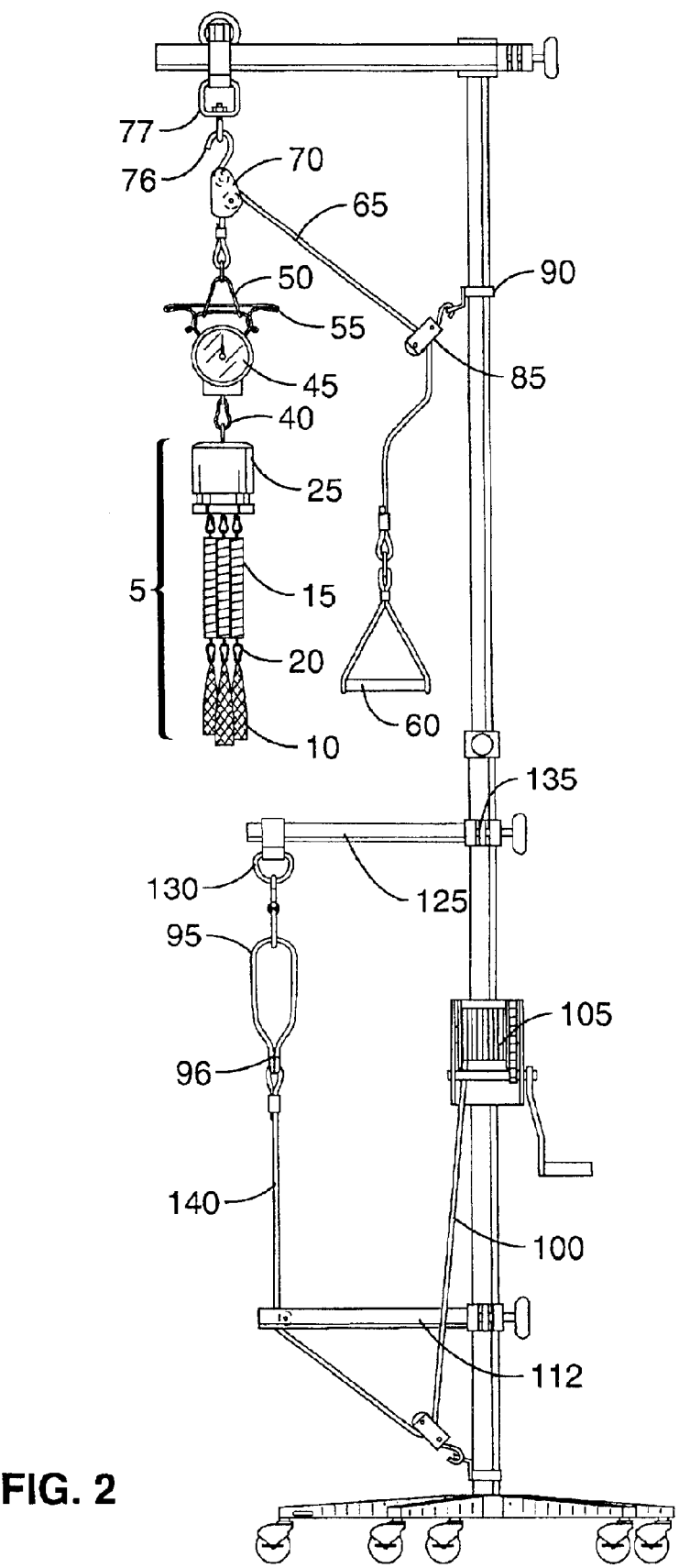
FIG. 2 is a front view of the subject invention showing a first embodiment of a second traction force generating means.
Figure 3:
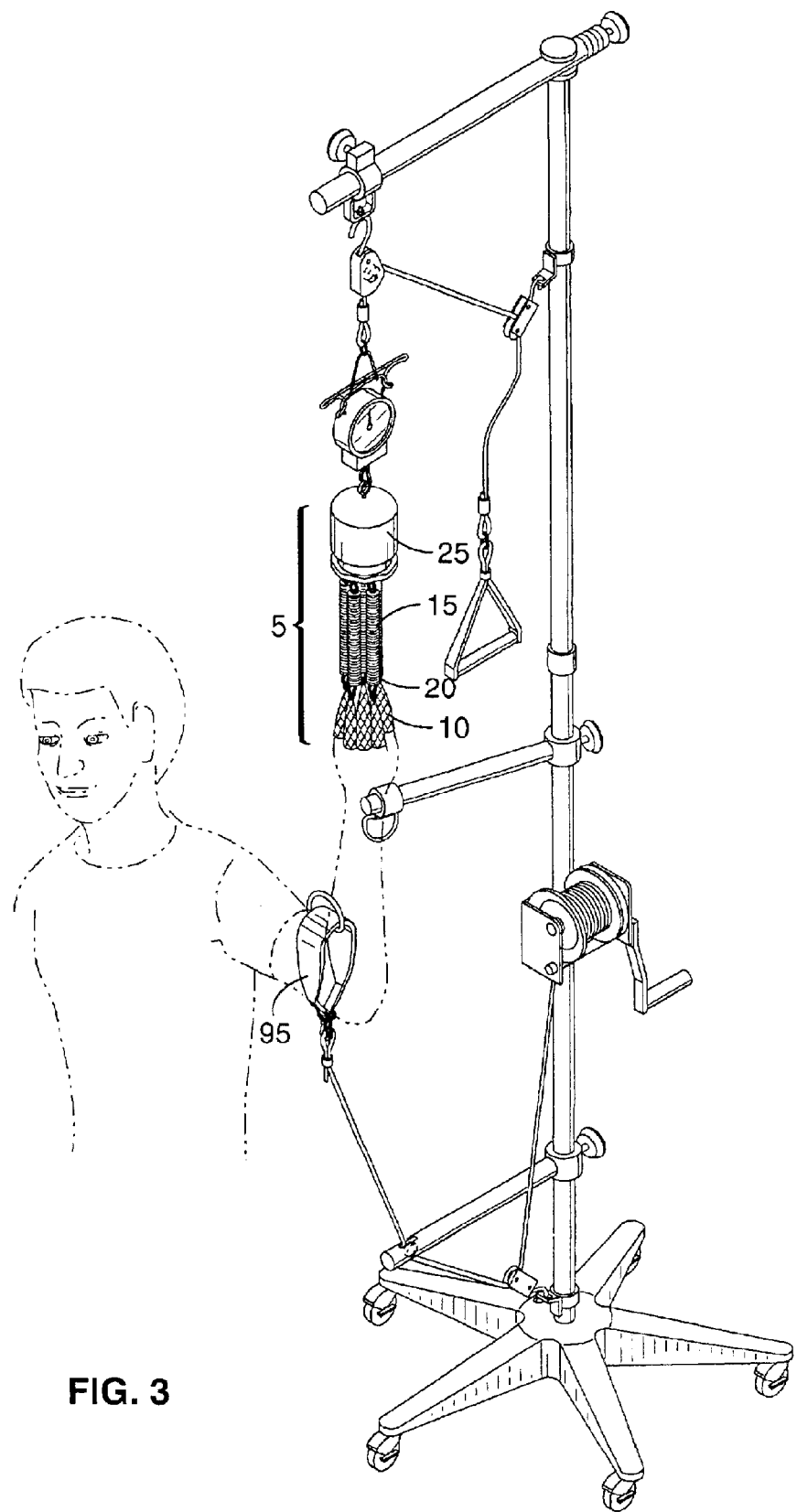
FIG. 3 is a perspective view of the subject invention, in association with a patient, showing a first embodiment of the second traction force generating means.
Figure 4:
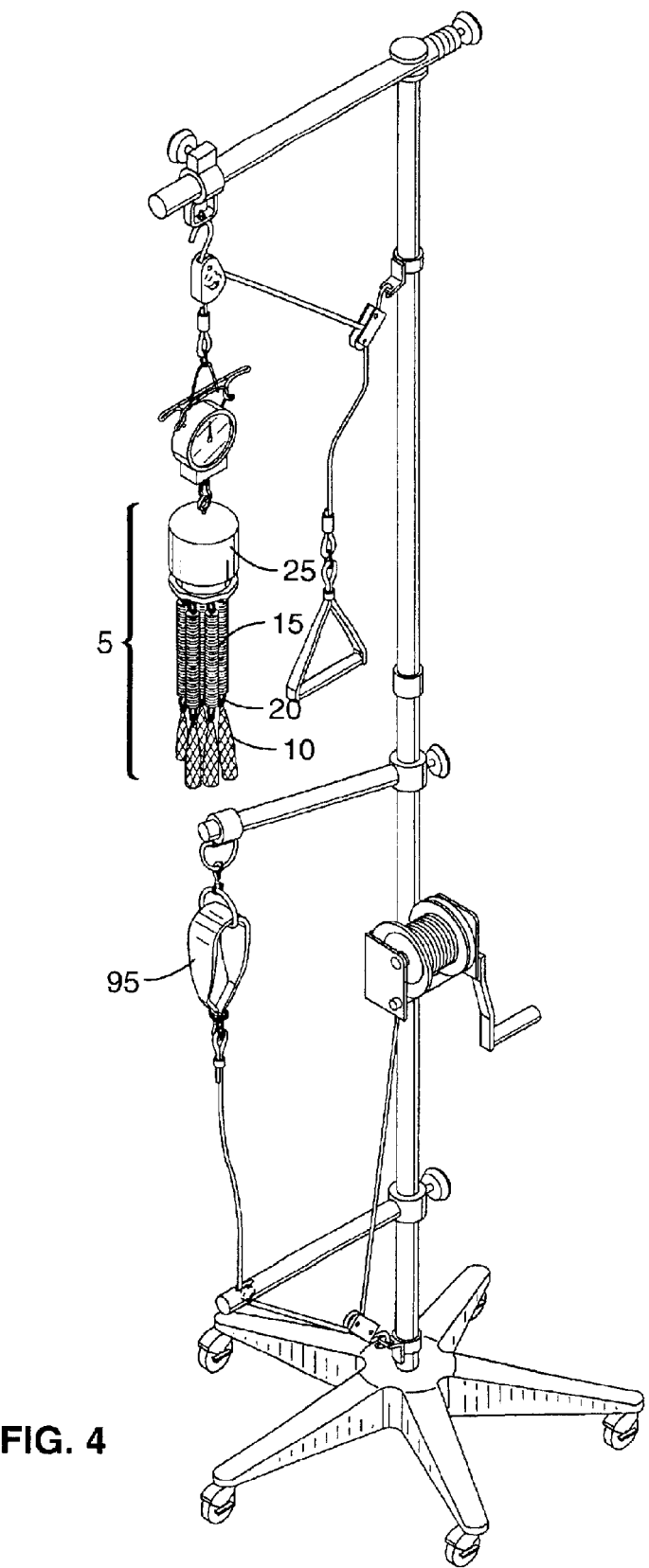
FIG. 4 is a perspective view of the subject invention showing a first embodiment of the second traction force generating means.
Figure 5:
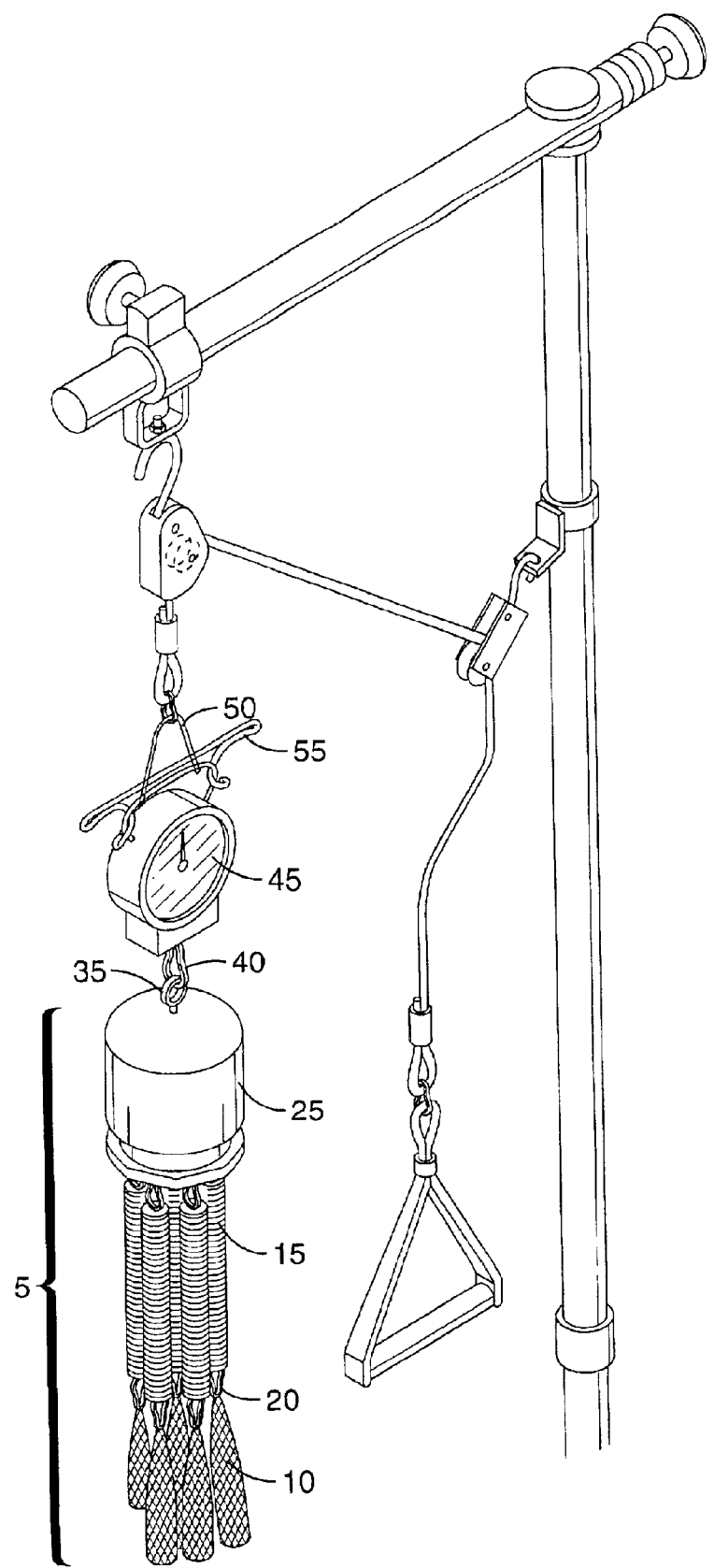
FIG. 5 is a perspective view of the subject traction assembly, traction force measurement means, first traction means, spacer, a portion of the support attachment means, and support.
Figure 6:
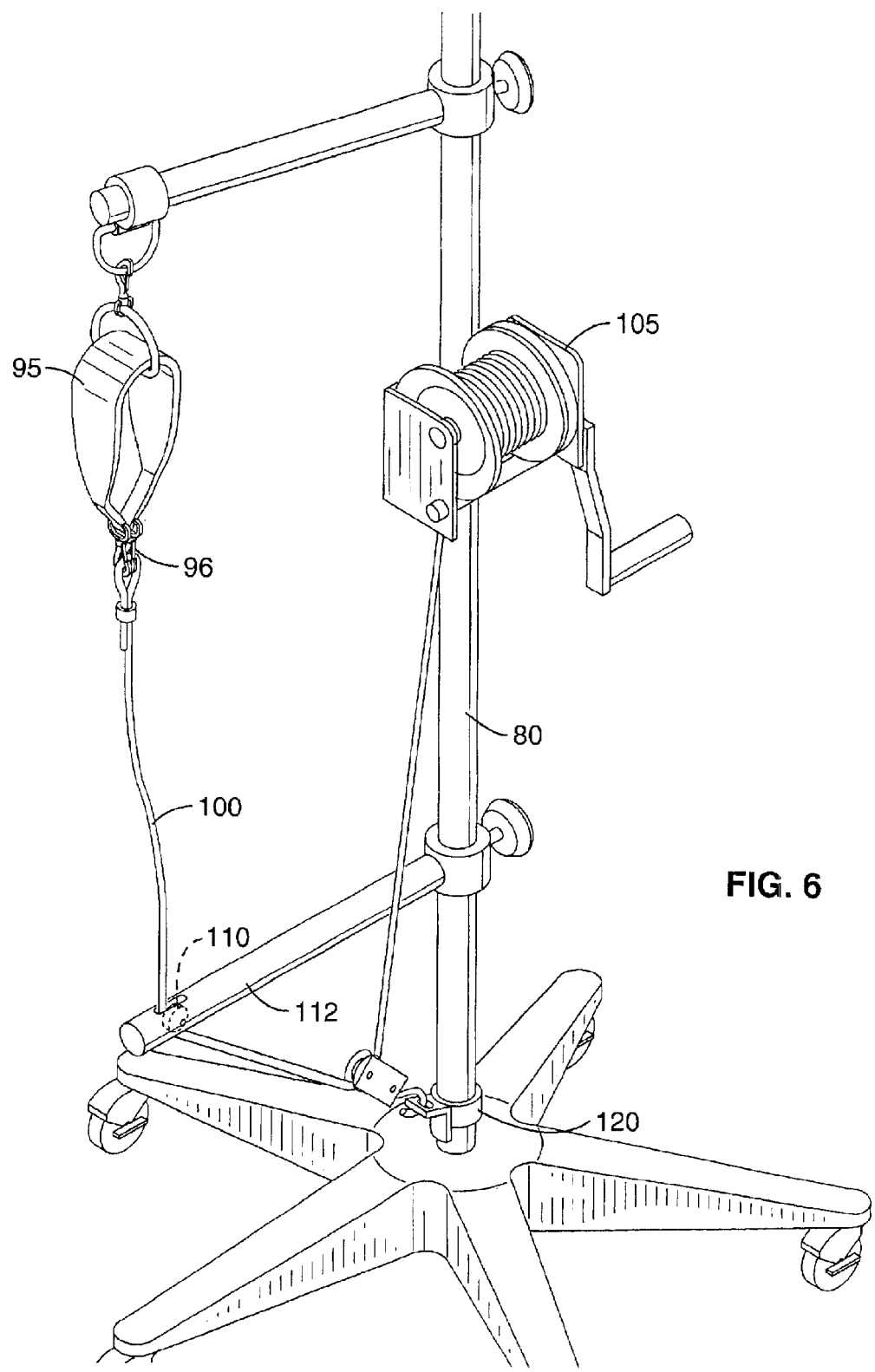
FIG. 6 is a perspective view of the subject invention showing the first embodiment of the second traction force generating means.

Referring now to FIGS. 1–9, there are shown preferred embodiments of a traction apparatus 1 for use in manipulating a patient's arm and wrist bones. The subject traction apparatus 1 comprises a traction assembly 5 (see FIGS. 1–5, 7A, 7B, and 8 and in particular see FIG. 5) that is itself composed of several components. To secure the subject device to the patient a plurality of finger traps 10 are provided. Each finger trap 10 is a standard finger cot that comprises a tapering cylinder of interlaced filaments that reversibly grip or tighten on a finger placed within the trap 10 and pulled away from the opposite end. Each finger is released by relieving the tension on the trap 10 and working the filaments loose (FIGS. 7A and 7B show a patient's fingers free and inserted, respectively). One end of each trap 10 is wide and open to receive a finger and the other end narrows to a fastening means such as a ring, loop, or similar device.

Further comprising the traction assembly 5 are a plurality of resilient means. Usually, each resilient means comprises a spring 15 or similar means such as an elastic member or the like. Each of the springs 15 is capable of releasably associating with at least one trap 10 by means of a releasable coupling such as a quick-release clip 20. For desirable traction purposes, more than one spring 15 may be connected to any trap 10 to increase the traction force.

Figure 8:
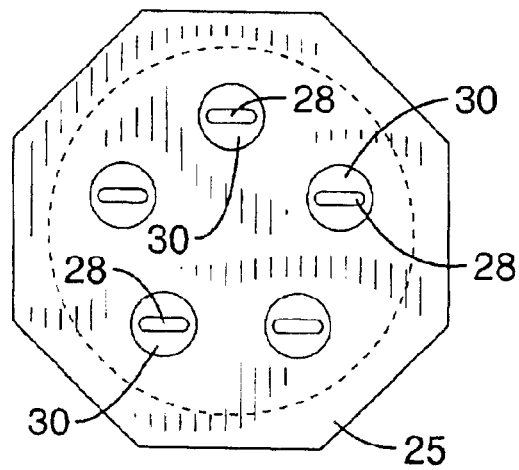
FIG. 8 is a bottom view of the swivel base of the traction assembly of the subject invention.
Figure 9:
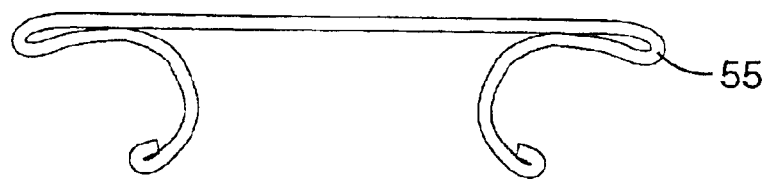
FIG. 9 is a side view of a finger spacer of the subject invention.

Also, comprising the traction assembly 5 is a swivel base 25 secured to each of said resilient means. The swivel base 25 is secured to one end of each spring 15 by suitable means. FIG. 8 depicts the bottom of the swivel base 25 and illustrates one suitable attachment means in which each spring end 28 fits within a receiving aperture 30 and is fastened in place by pinning means. Other suitable attachment means include, but are not limited to, quick-release clips, clamps, and the like. Preferably, to facilitate proper traction, the springs 15 are secured to the swivel base 25 is a generally circular attachment pattern (see FIG. 8).

Included in and projecting from the swivel base 25 is a swiveling attachment means 35 that allows the traction assembly 5 to swivel freely. The swivel attachment means 35 is usually an "eye" component (the "eye" presents a coupling aperture for securing to the remainder of the subject invention) rotationally secured in the swivel base 25.

Coupled to the traction assembly 5, via the swivel attachment means 35 and suitable clip/hook means 40, is a traction force measurement means 45. A suitable traction force measurement means 45 comprises an analog or digital scale or balance that, for example, may be a 50 lb scale to monitor the exact force applied to the patient's arm for traction purposes.

Figure 7B:
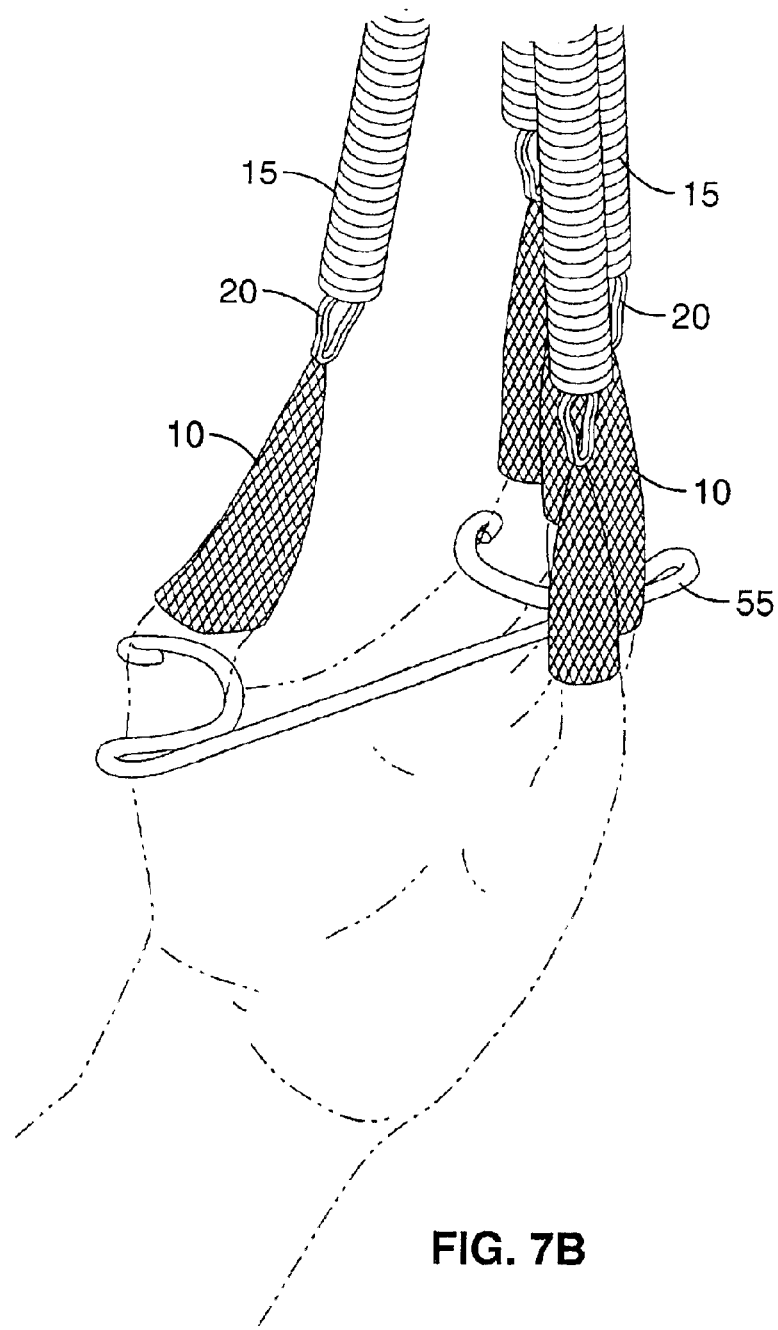
FIG. 7B is a perspective view showing a patient's hand, fitted with a finger spacer, after the patient's fingers are inserted into the subject finger traps.
Figure 7A:
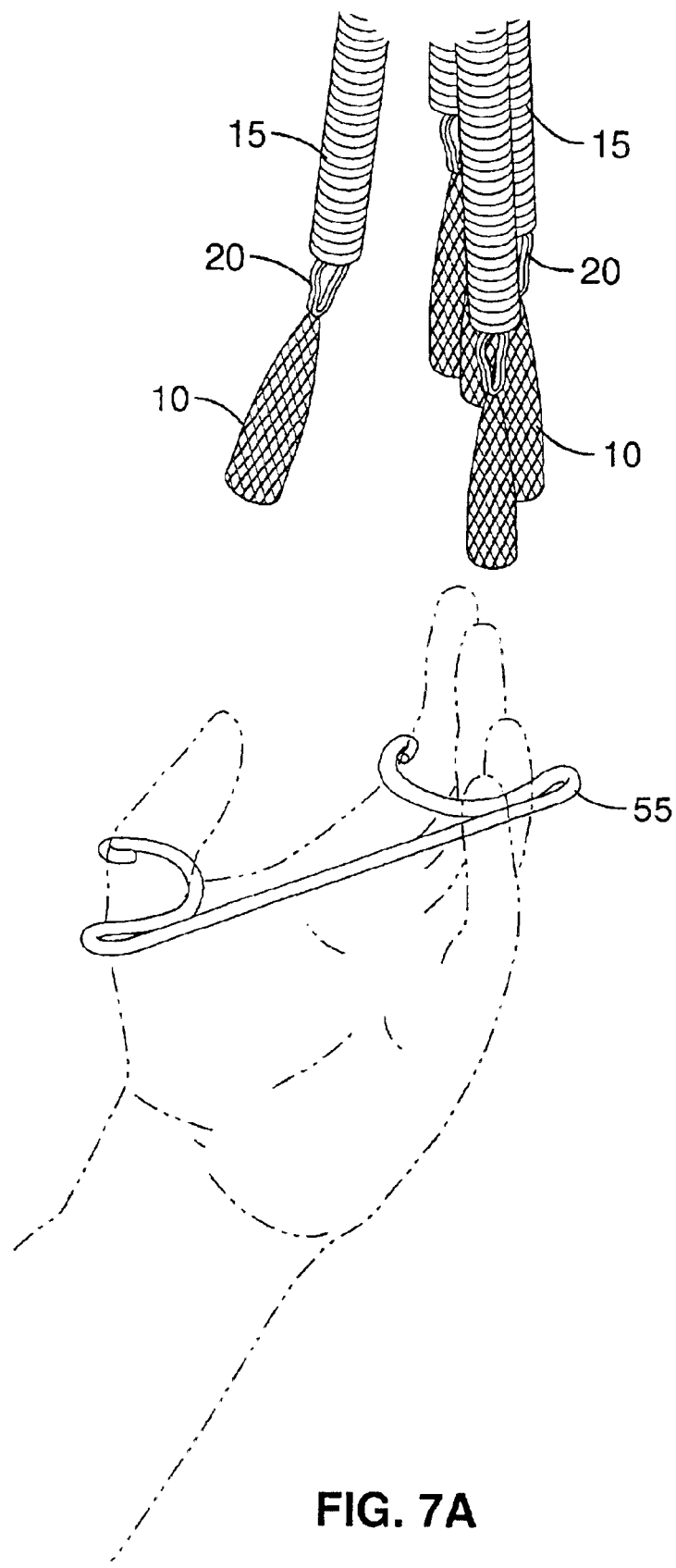
FIG. 7A is a perspective view showing a patient's hand, fitted with a finger spacer, before the patient's fingers are inserted into the subject finger traps.

Held in a suitable holder 50 is a finger spacer 55 utilized to position a patient's fingers during traction (FIGS. 7A and 7B show the spacer 55 in use). Although the holder 50 is depicted as being associated immediately on or proximate the traction force measurement means 45, other locations are contemplated as being within the realm of this disclosure. Having the holder 50 positioned proximate the traction force measurement means 45, as shown in the various figures, is a handy location, but should not be construed to preclude other mounting locations.

Secured to the traction force measurement means 45, either directly or indirectly via the holder 50, by suitable means such as a clip, hook, and the like, is a first traction force generating means. The first traction force generating means is used by the practitioner to apply a traction force to the patient's arm, via pulling on the fingers secured within the traps 10. Although equivalent variations are contemplated, one embodiment of the first traction force generating means comprises a first tension locking means that adjusts easily and has an easy grip handle 60 to apply a traction force. In particular, the first tension locking means comprises a cable 65 and ratchet 70. One end of the cable 65 is secured to the handle 60 and the other end of the cable 65 is secured to the traction force measurement means 45. The cable 65 interacts with the ratchet 70 to hold the cable 65 at a desired position. Usually, the ratchet 70 is releasably coupled to a horizontal support member 75 via suitable attachment means such as the depicted hook 76 and link 77. Additionally, the cable 65 is frequently associated with a vertical support 80 via a pulley 85 coupled or hooked to a suitable support anchor 90.

FIG. 1 illustrated two embodiments of a second traction force generating means that couples to the patient's upper arm. The second traction force generating means comprises an arm cuff 95, usually padded, that fits about the patient's upper arm (in particular see FIG. 3) and a second tension locking means secured to the arm cuff 95 that adjusts easily and has an easy grip means to apply a traction force. Two embodiments of the tension locking means are depicted in FIG. 1. A first embodiment is shown in detail in FIGS. 2, 3, 4, and 6 in which the arm cuff 95 is releasably coupled, by a clip, hook, or the like (usually a quick-release clip 96), to a cable 100 that extends to a crank-operated windlass 105 that reversibly locks. Usually, the cable 100 runs through a pulley means 110 associated with a lower horizontal support 112, secured to the vertical support 80, and through a pulley 115 that is hooked or coupled to a suitable support anchor 120. The patient's arm is inserted into the cuff 95 and the practitioner adjusts the tension locking means to a desired position by turning the crank on the windlass and engaging an associated lock. A horizontal support member 125, secured to the vertical support 80 with a suitable coupler 135, employing a suitable hook or coupler 130, is utilized to hold the cuff 95 when not in use.

In addition to the first embodiment, a second embodiment of the tension locking means is seen in FIG. 1 and comprises a cable 140, ratchet 145, and grip 150. The cable 140 is releasably secured to the arm cuff 95, via quick-release clip 96, and the cable 140 interacts with the ratchet 145 to hold the cable 140 at a desired position. As seen in FIG. 1, the first and second embodiments of the tension locking means may exist together or independently as desired.

The vertical support 80 is generally an IV poll or stand (thereby utilizing an existing medical facility structure) or other dedicated or equivalent structure that is capable of providing suitable support for the various components of the subject invention. Although the vertical support is usually a single structure, multiple equivalent constructs are contemplated. The support attachment means for securing the subject apparatus components to a vertical support 80 and associated horizontal supports 75, 112, and 125 were noted above and comprise releasable and adjustable means such as clamps and the like that grip the vertical support 80 is desired and usually adjustable positions.

The invention has now been explained with reference to specific embodiments. Other embodiments will be suggested to those of ordinary skill in the appropriate art upon review of the present specification.

Although the foregoing invention has been described in some detail by way of illustration and example for purposes of clarity of understanding, it will be obvious that certain changes and modifications may be practiced within the scope of the appended claims.

What is claimed is:

1. A traction apparatus for use in manipulating a patient's arm and wrist bones, comprising:
    a) a traction assembly, comprising:
        i) a plurality of finger traps;
        ii) a plurality of resilient means with each said resilient means capable of releasably associating with at least one said trap,
        iii) a swivel base secured to each of said resilient means;
        wherein each resilient means comprises:
            a) a spring having first and second ends;
            b) a first releasable coupling means associated with said first spring end and capable of releasably coupling with said finger trap; and
            c) a second coupling means associated with said second spring end capable of coupling with said swivel base;
    b) traction force measurement means coupled to said traction assembly;
    c) first traction force generating means linked to said traction force measurement means,
    d) second traction force generating means coupled to the patient's upper arm; and
    e) support attachment means for securing the subject apparatus components to a support.

2. An arm and wrist traction apparatus according to claim 1, wherein said first coupling means comprise a quick-release clip.

3. An arm and wrist traction apparatus according to claim 1, wherein said swivel base comprises:
    a) a first region secured to each of said plurality of resilient means and
    b) a second region coupled to said traction force measurement means.

4. An arm and wrist traction apparatus according to claim 3, wherein said plurality of resilient means are secured to said first region in a generally circular attachment pattern.

5. An arm and wrist traction apparatus according to claim 1, wherein said traction force measurement means comprises a scale.

6. An arm and wrist traction apparatus according to claim 1, wherein said first traction force generating means comprises a first tension locking means that adjusts easily and has an easy grip handle to apply a traction force.

7. An arm and wrist traction apparatus according to claim 6, wherein said first tension locking means comprises a cable and ratchet, wherein said cable is secured to said traction force measurement means and said cable interacts with said ratchet to hold said cable at a desired position.

8. An arm and wrist traction apparatus according to claim 1, wherein said second traction force generating means comprises:

a) an arm cuff that fits about the patient's upper arm and b) a second tension locking means secured to said arm cuff that adjusts easily and has an easy grip means to apply a traction force.

9. An arm and wrist traction apparatus according to claim 8, wherein said second tension locking means comprises a cable and ratchet, wherein said cable is secured to said arm cuff and said cable interacts with said ratchet to hold said cable at a desired position.

10. An arm and wrist traction apparatus according to claim 1, wherein said support attachment means comprises:

a) first clamping means for securing said traction assembly, said traction force measurement means, and said first traction force generating means to said support and b) second clamping means for securing said second traction force generating means to said support.

11. An arm and wrist traction apparatus according to claim 1, further comprising a spacer for separating and positioning the patient's fingers.

12. An traction apparatus for use in manipulating a patient's arm and wrist bones, comprising:

a) a traction assembly, comprising:

i) a plurality of finger traps;

ii) a plurality of resilient means with each said resilient means capable of releasably associating with at least one said trap, wherein each resilient means comprises:

a spring having first and second ends;

a first releasable coupling means associated with said first spring end and capable of releasably coupling with said finger trap; and a second coupling means associated with said second spring end capable of coupling with said swivel base; and iii) a swivel base secured to each of said resilient means;

b) traction force measurement means coupled to said traction assembly;

c) first traction force generating means linked to said traction force measurement means;

d) second traction force generating means coupled to the patient's upper arm; and e) support attachment means for securing the subject apparatus components to a support.

13. An arm and wrist traction apparatus according to claim 12, wherein said first coupling means comprise a quick-release clip.

14. An arm and wrist traction apparatus according to claim 12, wherein said swivel base comprises:

a) a first region secured to each of said plurality of resilient means and b) a second region coupled to said traction force measurement means.

15. An arm and wrist traction apparatus according to claim 14, wherein said plurality of resilient means are secure to said first region in a generally circular attachment pattern.

16. An arm and wrist traction apparatus according to claim 12, wherein said traction force measurement means comprises a scale.

17. An arm and wrist traction apparatus according to claim 12, wherein said first traction force generating means comprises a first tension locking means that adjusts easily and has an easy grip handle to apply a traction force.

18. An arm and wrist traction apparatus according to claim 17, wherein said first tension locking means comprises a cable and ratchet, wherein said cable is secured to said traction force measurement means and said cable interacts with said ratchet to hold said cable at a desired position.

19. An arm and wrist traction apparatus according to claim 12, wherein said second traction force generating means comprises:

a) an arm cuff that fits about the patient's upper arm and b) a second tension locking means secured to said arm cuff that adjusts easily and has an easy grip means to apply a traction force.

20. An arm and wrist traction apparatus according to claim 19, wherein said second tension locking means comprises a cable and ratchet, wherein said cable is secured to said arm cuff and said cable interacts with said ratchet to hold said cable at a desired position.

21. An arm and wrist traction apparatus according to claim 12, wherein said support attachment means comprises:

a) first clamping means for securing said traction assembly, said traction force measurement means, and said first traction force generating means to said support and b) second clamping means for securing said second traction force generating means to said support.

22. An arm and wrist traction apparatus according to claim 12, further comprising a spacer for separating and positioning the patient's fingers.

* * * * *